(12) United States Patent
Uematsu et al.

(10) Patent No.: US 11,618,873 B2
(45) Date of Patent: Apr. 4, 2023

(54) CULTURE INSTRUMENT

(71) Applicant: HITACHI HIGH-TECHNOLOGIES CORPORATION, Tokyo (JP)

(72) Inventors: Chihiro Uematsu, Tokyo (JP); Hiroko Fujita, Tokyo (JP); Akira Masuya, Tokyo (JP)

(73) Assignee: HITACHI HIGH-TECH CORPORATION, Tokyo (JP)

(*) Notice: Subject to any disclaimer, the term of this patent is extended or adjusted under 35 U.S.C. 154(b) by 233 days.

(21) Appl. No.: 16/464,830

(22) PCT Filed: Dec. 14, 2016

(86) PCT No.: PCT/JP2016/087301
§ 371 (c)(1),
(2) Date: May 29, 2019

(87) PCT Pub. No.: WO2018/109886
PCT Pub. Date: Jun. 21, 2018

(65) Prior Publication Data
US 2019/0292505 A1   Sep. 26, 2019

(51) Int. Cl.
*C12M 1/32* (2006.01)
*C12M 1/00* (2006.01)
(Continued)

(52) U.S. Cl.
CPC ............. *C12M 23/12* (2013.01); *C12M 1/34* (2013.01); *C12M 23/22* (2013.01); *C12M 23/38* (2013.01); *C12M 37/00* (2013.01)

(58) Field of Classification Search
CPC ...... C12M 23/12; C12M 23/22; C12M 23/38; C12M 1/34; C12M 37/00
(Continued)

(56) References Cited

U.S. PATENT DOCUMENTS 4,720,463 A   1/1988 Farber et al.
5,141,718 A * 8/1992 Clark ..................... C12M 23/12
                                                        435/297.5
(Continued)

FOREIGN PATENT DOCUMENTS

CN   102719352 B   1/2014
JP   61-247373 A   11/1986
(Continued)

OTHER PUBLICATIONS

WO2015198866A1—Toshihiro et al. Machine English Translation (Year: 2015).*
(Continued)

*Primary Examiner* — Michael L Hobbs
*Assistant Examiner* — Lenora A Abel
(74) *Attorney, Agent, or Firm* — Mattingly & Malur, PC

(57) ABSTRACT

A culturing device includes a microplate including a plurality of vessels, each of the vessels having a bottom surface having light transmittance and an opening at an upper portion, a lid having light transmittance, and an intermediate plate having light transmittance sandwiched between the lid and the microplate. The intermediate plate has a plurality of convex portions on a surface thereof facing the microplate and provided with a plurality of through holes corresponding to the convex portions that are disposed so that when the intermediate plate and the microplate are overlapped, each of the plurality of convex portions is inserted into each of the plurality of vessels and each of the plurality of through holes coincides with the opening of each of the plurality of vessels. The lid comes into contact with the intermediate plate so as to close the plurality of through holes provided in the intermediate plate.

7 Claims, 9 Drawing Sheets

(51) Int. Cl.
*C12M 1/12* (2006.01)
*C12M 1/34* (2006.01)

(58) Field of Classification Search
USPC ..................................................... 435/305.3
See application file for complete search history.

(56) References Cited

U.S. PATENT DOCUMENTS

| | | | |
|---|---|---|---|
| 5,366,893 A * | 11/1994 | Stevens | B01L 3/50851 |
| | | | 422/536 |
| 5,728,350 A * | 3/1998 | Kinoshita | C12Q 1/00 |
| | | | 422/412 |
| 2005/0239197 A1 | 10/2005 | Katerkamp et al. | |
| 2009/0082600 A1 * | 3/2009 | Zhou | C12P 7/06 |
| | | | 568/840 |
| 2012/0082600 A1 * | 4/2012 | Esser | C12M 25/04 |
| | | | 422/552 |
| 2014/0322806 A1 * | 10/2014 | Bennett | C12N 5/0602 |
| | | | 435/325 |
| 2016/0250632 A1 | 9/2016 | Hong et al. | |
| 2017/0051241 A1 | 2/2017 | Obi et al. | |
| 2017/0067006 A1 | 3/2017 | Obi et al. | |

FOREIGN PATENT DOCUMENTS

| | | |
|---|---|---|
| JP | 2002-538833 A | 11/2002 |
| JP | 3104790 U | 8/2004 |
| JP | 2005-516596 A | 6/2005 |
| JP | 2007-300853 A | 11/2007 |
| JP | 5768174 B1 | 8/2015 |
| JP | 2016-026474 A | 2/2016 |
| JP | 2016-041042 A | 3/2016 |
| JP | 2016-054655 A | 4/2016 |
| WO | 00/55357 A1 | 9/2000 |
| WO | WO-2015198866 A1 * 12/2015 ............ C12M 29/20 |
| WO | 2016/137341 A1 | 9/2016 |
| WO | 2016/138338 A1 | 9/2016 |

OTHER PUBLICATIONS

Japanese Office Action received in corresponding Japanese Application No. 2018-556108 dated Oct. 13, 2020.
International Search Report of PCT/JP2016/087301 dated Feb. 7, 2017.
Supplemental European Search Report received in Application No. EP 16924151.0 dated Jun. 24, 2020.
Japanese Office Action received in corresponding Japanese Application No. 2018-556108 dated Jun. 2, 2020.
Chinese Office Action received in corresponding Chinese Application No. 201680091212.2 dated Mar. 21, 2022.

* cited by examiner

FIG. 1
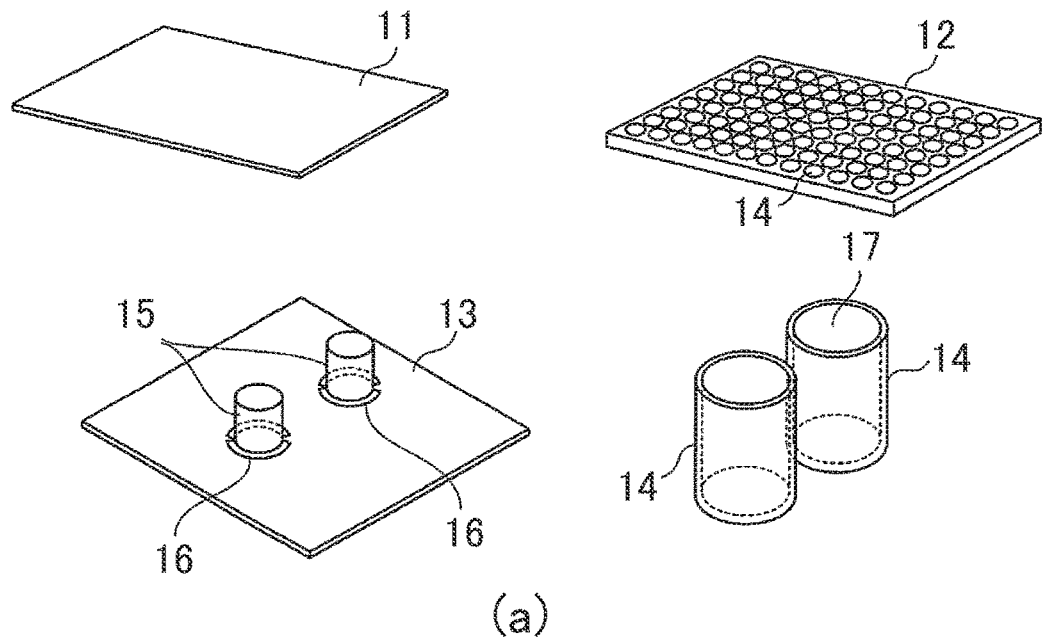
(a)
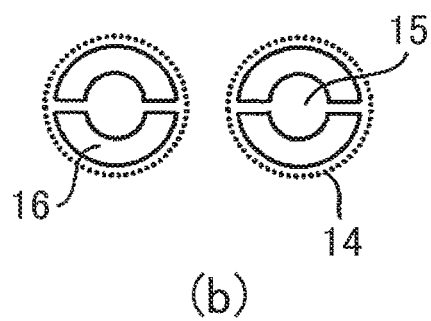
(b)
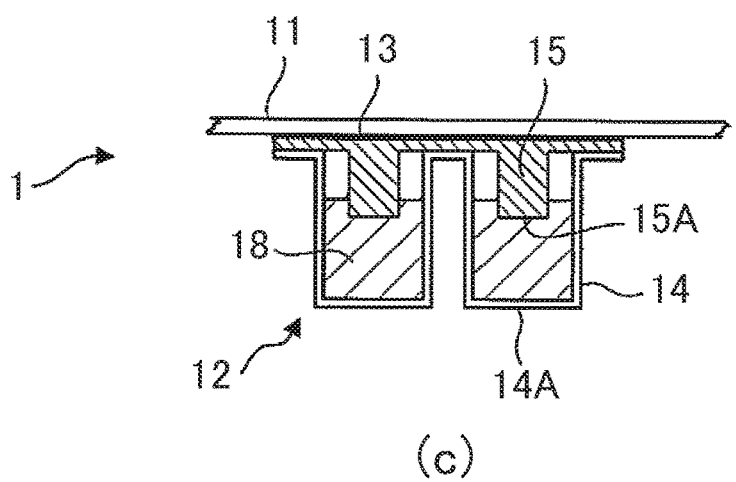
(c)

FIG. 5
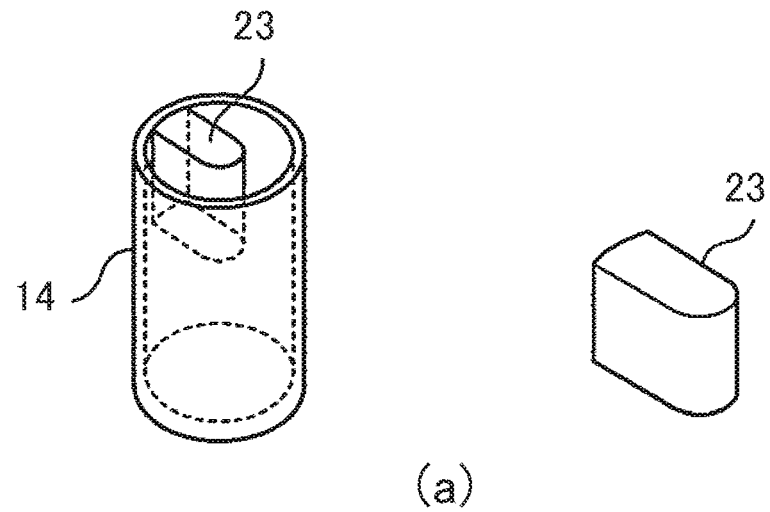
(a)
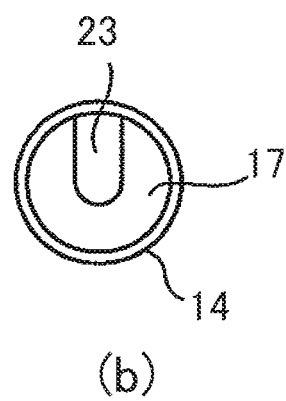
(b)
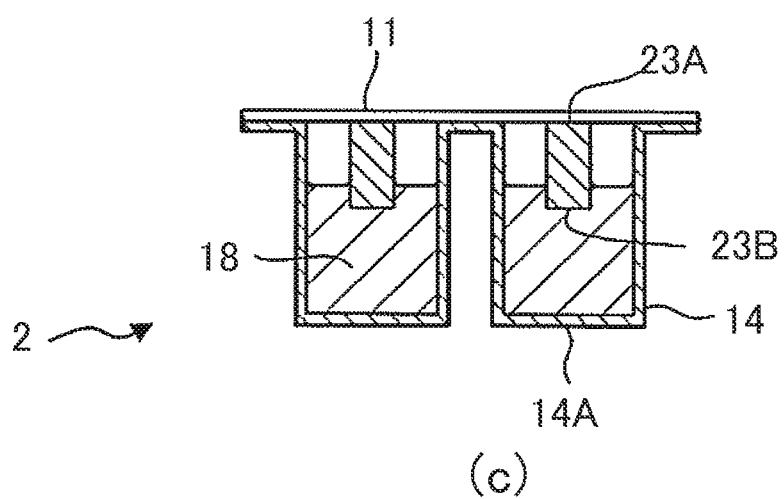
(c)

FIG. 6
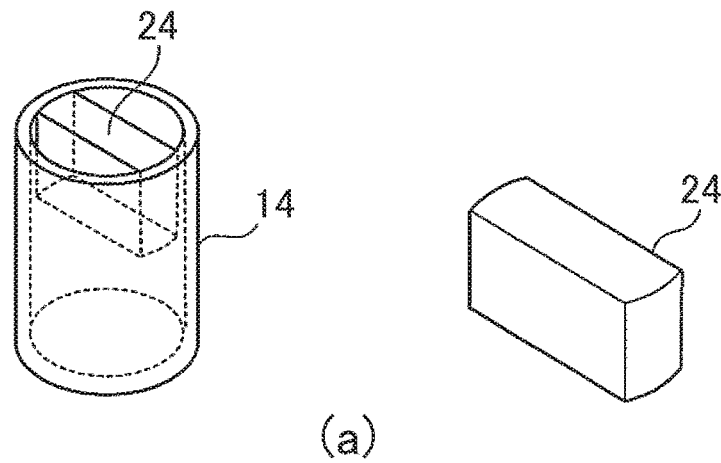
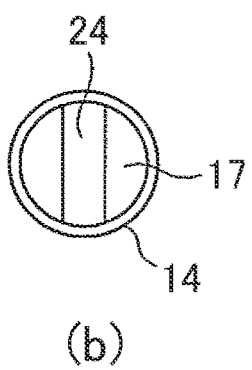
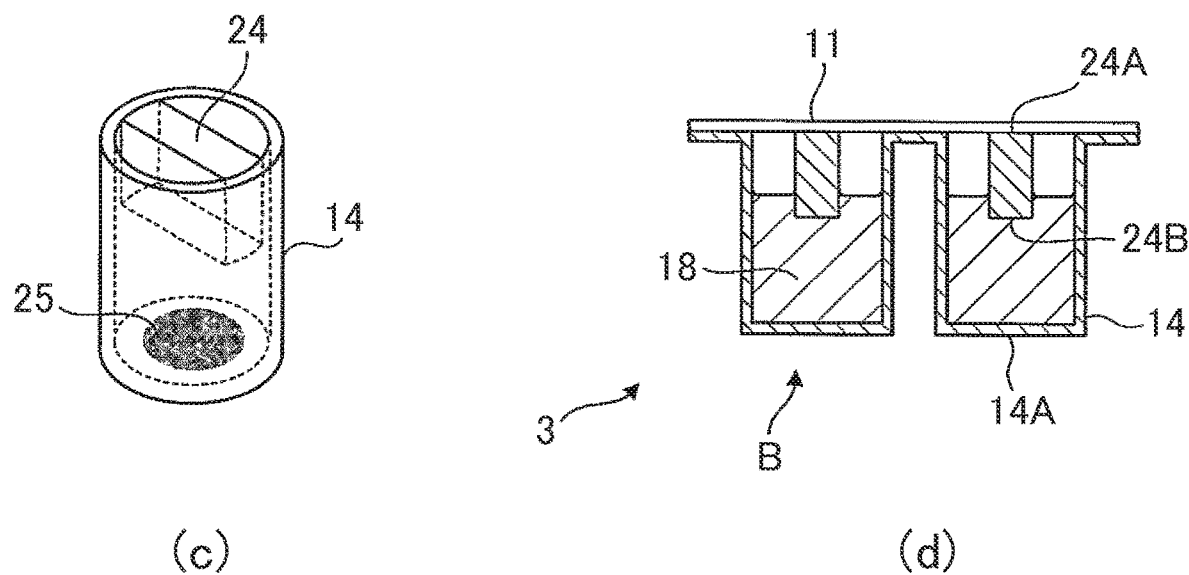

FIG. 7
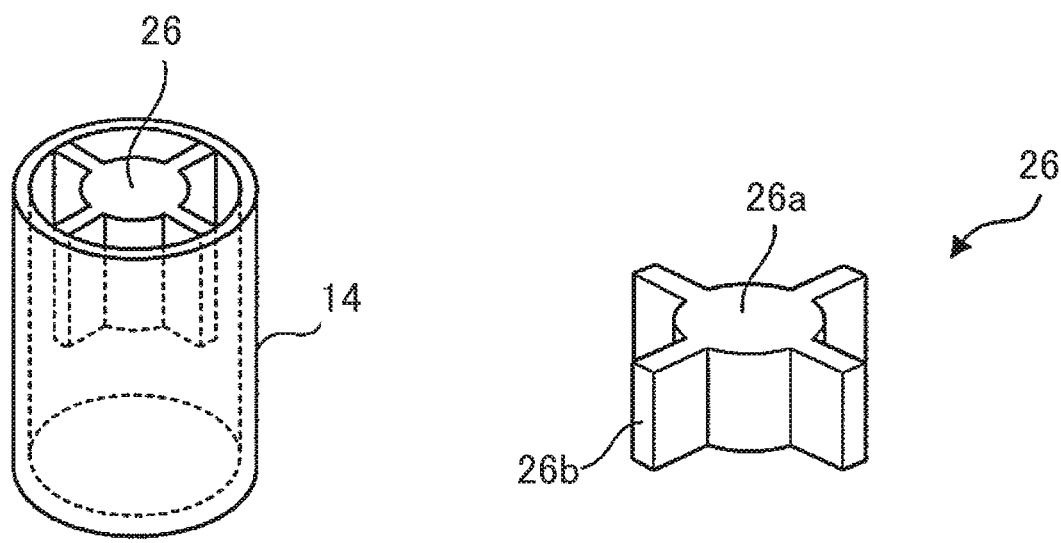
(a)
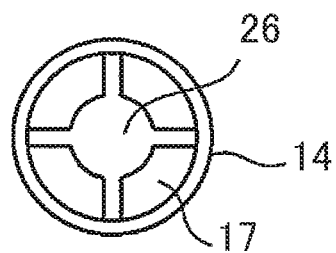
(b)

CULTURE INSTRUMENT

TECHNICAL FIELD

This disclosure relates to a culturing device used for examining bacteria, fungi, and the like.

BACKGROUND ART

Conventionally, a culture medium and cells are introduced into a culture vessel to culture the cells. When the cells are cultured, a lid is disposed on the culture vessel for the purpose of the prevention of the infection of the cells with bacteria, the inhibition of the increase in the pH of the culture medium, and the like. The observation of the change in the form with time, the motility, the invasive ability, and the like of the culture cells is often performed while the lid is disposed on the culture vessel.

To completely prevent dew condensation on a microscope observation portion in the interior of a culture lid and to inhibit the change in the amount used and the pH of a culture medium, Patent Literature 1 discloses a cell incubator for microscope including a culture dish and a lid provided in its center portion with a recessed portion.

CITATION LIST

Patent Literature

Patent Literature 1: Japanese Unexamined Utility Model Application Publication No. 3104790

SUMMARY OF INVENTION

Technical Problem

In using the cell culture vessel for microscope described in Patent Literature 1, when the operation of adding a reagent to the culture medium or extracting part of the culture medium is performed, the lid is required to be removed. Here, since the recessed portion of the lid is immersed into the culture medium, the culture medium adheres to the lid removed from the culture vessel.

Therefore, when the cell culture vessel for microscope according to Patent Literature 1 is applied to the well of the microplate, there is a possibility that, into the well, the culture medium from the adjacent well having different culture conditions is mixed at the time of performing the operation of removing the lid. On the other hand, when the opening is simply provided in the lid to eliminate the operation of removing the lid, the infection with bacteria cannot be prevented.

This disclosure has been made in view of the above points, and provides a culturing device where an interior of each of culture vessels can be observed with high accuracy and that can reduce a risk of contamination.

Solution to Problem

This disclosure includes a plurality of means for solving the above problems, and as an example, provides a culturing device including a microplate having a plurality of vessels, each of the vessels having a bottom surface having light transmittance and having an opening at an upper portion, a lid having light transmittance and covering an upper surface of the microplate, and an intermediate plate having light transmittance and being sandwiched between the lid and the microplate, the intermediate plate having a plurality of convex portions on a surface of the intermediate plate facing the microplate, provided with a plurality of through holes corresponding to the plurality of convex portions. The plurality of convex portions and the plurality of through holes are disposed so that when the intermediate plate and the microplate are overlapped, each of the plurality of convex portions is inserted into each of the plurality of vessels and each of the plurality of through holes coincides with the opening of each of the plurality of vessels. The lid comes into contact with the intermediate plate so as to close the plurality of through holes provided in the intermediate plate.

As another example solving the above problems, this disclosure provides a culturing device including a microplate including a plurality of vessels, each of the plurality of vessels having a bottom surface having light transmittance and into which a component is attached, the component extending from an upper end of the vessel to an interior of the vessel so as to have an opening and having light transmittance, and a lid having light transmittance and covering an upper surface of the microplate. The component has two surfaces substantially parallel to the bottom surface of the vessel, one of the two faces being located at the same height as the upper surface of the microplate or at a position higher than the upper surface of the microplate.

Advantageous Effects of Invention

According to this disclosure, the observation of the interior of each of the culture vessels can be performed satisfactorily, and the risk of contamination can be reduced. Objects, configurations and effects other than the above will be apparent from the description of the following embodiments.

BRIEF DESCRIPTION OF DRAWINGS

FIG. 1 is a diagram of assistance in explaining the configuration of a culturing device according to a first embodiment.

FIG. 5 is a diagram of assistance in explaining the configuration of a culturing device according to a second embodiment.

FIG. 6 is a diagram of assistance in explaining the configuration of a culturing device according to a third embodiment.

FIG. 7 is a diagram illustrating another example of a component pressed into the vessel.

DESCRIPTION OF EMBODIMENTS

Overview

Figure 2:
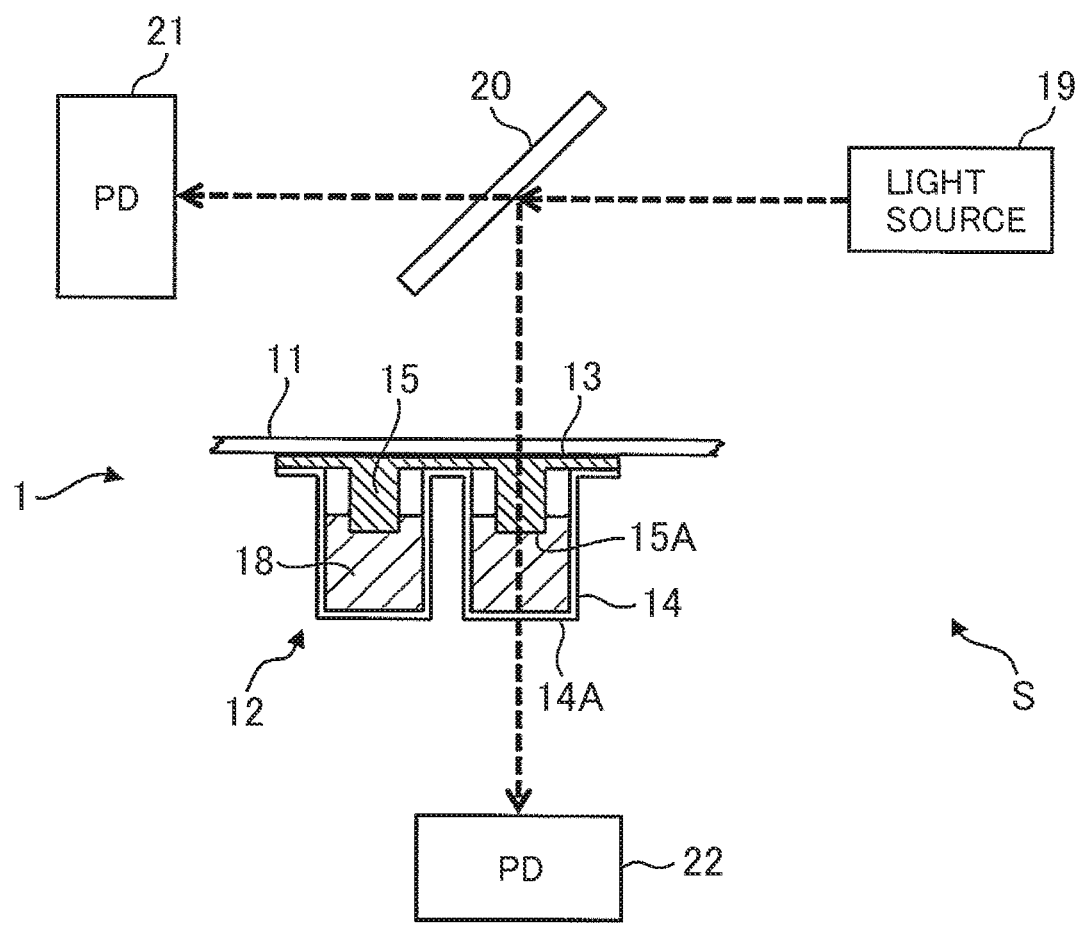
FIG. 2 is a diagram of assistance in explaining an optical system for measuring turbidity.

When cells are cultured by using a culturing device, a lid is typically disposed so as to close an opening of each of vessels in order to prevent the intrusion of bacteria and the like. Since the cells are cultured at temperatures of approximately 30° C. to 35° C., a culture medium is evaporated to often fog the lid. The fogging of the lid causes trouble in observing an interior of the vessel, and for example, it is difficult to precisely measure turbidity of the culture medium.

In the culturing device of this disclosure, an intermediate plate or a component having light transmittance is sandwiched between the lid and the culture medium, so that the lid is not fogged at a position above each of convex portions included in the intermediate plate or above the component. Therefore, in the culturing device of this disclosure, the interior of the vessel can be observed through part of the lid.

The intermediate plate or the component is configured not to cover the entire opening of the vessel. For that, in the culturing device of this disclosure, a reagent can be injected into the interior of the vessel even without removing the intermediate plate or the component. Therefore, unlike a case where the lid to which a large amount of the culture medium adheres is removed to inject the reagent, in the culturing device of this disclosure, a risk of contamination can be reduced. Also, in the culturing device of this disclosure, part of the member is immersed into the culture medium, so that the interior of the vessel can be observed satisfactorily through the lid and the member.

Various embodiments of this disclosure will be described below with reference to the accompanying drawings. However, these embodiments are illustrative only for achieving the present invention, and do not limit the technical range of this disclosure. Also, the configurations shared among the respective drawings are indicated by the same reference numerals.

First Embodiment

The Configuration of a Culturing Device

FIG. 1 is a diagram of assistance in explaining the configuration of a culturing device 1 according to a first embodiment. The culturing device 1 includes a lid 11, a microplate 12 and an intermediate plate 13. FIG. 1(a) is a perspective view illustrating the lid 11, the microplate 12, a portion enlargedly illustrating a surface of the intermediate plate 13 coming into contact with the microplate 12, and vessels 14 included in the microplate 12.

The shape of the lid 11 is substantially planar, and one of surfaces of the lid 11 comes into contact with one of surfaces of the intermediate plate 13. The lid 11 has light transmittance, and covers an upper surface of the microplate 12.

The microplate 12 includes a plurality of the vessels 14 each having an opening at an upper portion. Each of the vessels 14 accommodates a culture medium and the like. In the example illustrated in FIG. 1(a), the microplate 12 includes a total of 96 vessels 14 arrayed in 12 columns by 8 rows.

The intermediate plate 13 is used by being sandwiched between the lid 11 and the microplate 12. The intermediate plate 13 has a plurality of convex portions 15 on the surface of the intermediate plate 13 facing the microplate 12, and in a periphery of each of the plurality of convex portions 15, each of a plurality of through holes 16 is provided. In FIG. 1(a), only two of the plurality of convex portions 15 are illustrated, but for example, the plurality of convex portions 15 equal in number to that of the vessels 14 included in the microplate 12 are provided on the intermediate plate 13.

The plurality of convex portions 15 and the plurality of through holes 16 included in the intermediate plate 13 are disposed so that when the intermediate plate 13 and the microplate 12 are overlapped, each of the plurality of convex portions 15 is inserted into each of the plurality of vessels 14 and each of the plurality of through holes 16 coincides with an opening 17 of each of the plurality of vessels 14. The lid 11 comes into contact with the intermediate plate 13 so as to close the plurality of through holes 16 provided in the intermediate plate 13.

FIG. 1(b) is a diagram illustrating a state of an upper surface of each of the vessels 14 when the microplate 12 and the intermediate plate 13 are overlapped. In the example illustrated in FIG. 1(b), each of the convex portions 15 of the intermediate plate 13 is disposed so as to be located at a center of the vessel 14. Also, the opening 17 of the vessel 14 included in the microplate 12 is not completely covered due to the presence of each of the through holes 16 included in the intermediate plate 13 in a state where the lid 11 is not overlapped with the intermediate plate 13. Therefore, the interior of each of the vessels 14 can be accessed through the through hole 16.

In the culturing device 1, a liquid can be added and suctioned from the through hole 16 of the intermediate plate 13 by removing the lid 11. For example, a reagent for identifying bacteria can be injected from the through hole 16 into each of the vessels 14. When the culture medium is changed in color after the injection of the reagent, it is possible to determine that bacteria grow in the culture medium.

Examples of the reagent added to the vessel 14 include a Kovac's reagent for determining that indole has been generated, sodium hydroxide and a-naphthol for determining a VP (Voges-Proskauer) reaction, a sulfanilic acid and an a-naphthylamine solution for determining a silver nitrate reducibility, phenol red, bromocresol purple, and bromothymol blue that are pH indicators, and the like.

FIG. 1(c) is a side cross-sectional view illustrating a state where each of the plurality of vessels 14 accommodates a culture medium 18, and the lid 11, the microplate 12 and the intermediate plate 13 are overlapped. As illustrated in FIG. 1(c), each of the plurality of convex portions 15 has a surface 15A substantially parallel to a bottom surface 14A of each of the plurality of vessels 14 when the intermediate plate 13 is overlapped with the microplate 12.

As illustrated in FIG. 1(c), for example, a length of the convex portion 15 is adjusted so that the surface 15A is immersed into the culture medium 18. Also, of the surfaces that the intermediate plate 13 has, the surface coming into contact with the lid 11 is located at a position higher than an upper edge of the opening 17 of the vessel 14. The lid 11 and the intermediate plate 13 are in substantially contact with each other without sandwiching an air layer, or the lid 11 and the portion of the intermediate plate 13 having the convex portion 15 are in contact with each other without sandwiching an air layer. Therefore, when the culturing device 1 is used, the light is prevented from being refracted, so that the interior of the vessel 14 can be observed satisfactorily.

In the culturing device 1 of this disclosure, to achieve desired optical measurement, the lid 11, the intermediate plate 13 and at least the bottom surface 14A portion of each of the vessels 14 of the microplate 12 are formed of a material having light transmittance. Examples of the material having light transmittance used for the culturing device 1 of this disclosure include, for example, polypropylene, polystyrene, and polycarbonate.

The effects exhibited by the culturing device 1 according to the first embodiment In the culturing device 1 according to the first embodiment, each of the lid 11 and the intermediate plate 13 has light transmittance. Also, when a position of a liquid level of the culture medium 18 is located at a position where the surface 15A of each of the convex portions 15 is immersed, the surface 15A of the convex portion 15 is not fogged due to the dew condensation of the evaporated culture medium 18. Further, a portion of the lid 11 located on an upper portion of the convex portion 15 of the intermediate plate 13 is not fogged. Therefore, when the culturing device 1 according to the first embodiment is used, the interior of each of the vessels 14 can be observed satisfactorily through the surface 15A even in the state where the lid 11 and the intermediate plate 13 are overlapped with the microplate 12.

Also, in the microplate 12, at least the bottom surface 14A of each of the vessels 14 is formed of the material having light transmittance, so that the culturing device 1 of this disclosure can measure the turbidity of the culture medium 18 accommodated in the vessel 14 by using a dichroic mirror and a photodiode.

Also, in each of the plurality of vessels 14, each of the through holes 16 coincides with the opening 17 in the state where the intermediate plate 13 is overlapped with the microplate 12. Therefore, in the culturing device 1, the injection of the reagent and the extraction of the culture medium are enabled from the through hole 16 by removing the lid 11 even without removing the intermediate plate 13 to which a large amount of the culture medium 18 adheres. Therefore, in the culturing device 1, the culture medium 18 having different ingredients can be prevented from mixing into each other.

The configuration of an optical system for the measurement of turbidity

FIG. 2 is a diagram of assistance in explaining an optical system S for measuring turbidity. The optical system S includes a light source 19, a dichroic mirror 20, a first photodiode (PD) 21, a second photodiode (PD) 22 and the culturing device 1.

Part of a light emitted from the light source 19 transmits through the dichroic mirror 20, and another part of the light is reflected by the dichroic mirror 20. The light transmitted through the dichroic mirror 20 is detected by the first photodiode 21. The light reflected by the dichroic mirror 20 transmits through the lid 11, the intermediate plate 13, the culture medium 18 and the bottom surface 14A of each of the vessels 14 of the culturing device 1, and is detected by the second photodiode 22. The turbidity of the culture medium 18 can be measured by comparing the light amount detected by the first photodiode 21 and the light amount detected by the second photodiode 22. It should be noted that in the optical system S, the dichroic mirror 20 may be a semi-transparent mirror.

Figure 3:
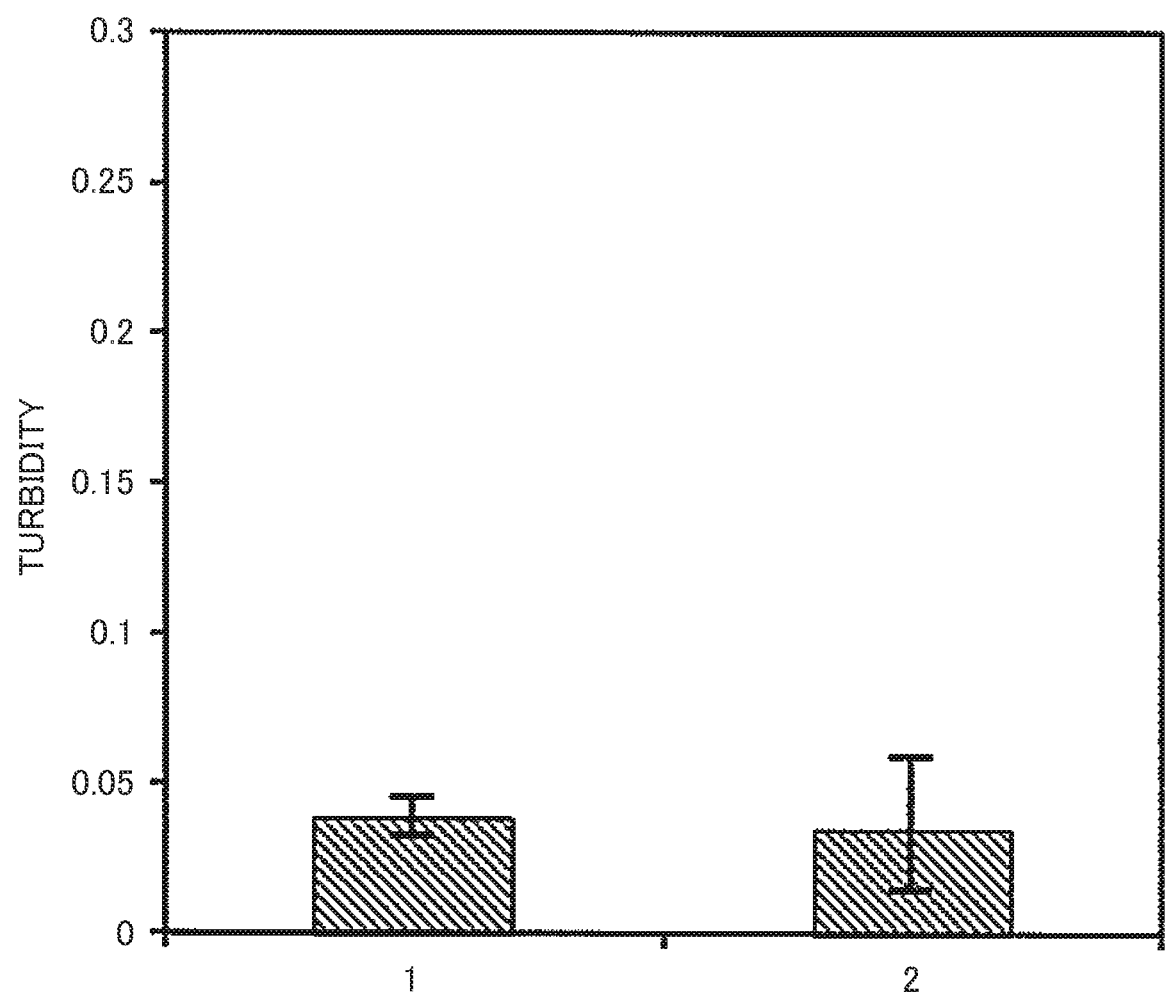
FIG. 3 is a diagram comparing measurement results of turbidity.

FIG. 3 is a diagram comparing the measurement results of turbidity. In FIG. 3, series 1 is a result of the turbidity measurement using the culturing device 1 according to the first embodiment, and series 2 is a result of the turbidity measurement using a conventional culturing device without the intermediate plate 13. As illustrated in FIG. 3, in the culturing device 1 of this disclosure, since no dew condensation occurs on the lid 11, it is found that the measurement result does not vary.

First Modification

In the above description, the microplate 12 includes the 96 vessels 14, but the number of the vessels 14 included in the microplate 12 is not limited to the above value. The microplate 12 can include an arbitrary number of vessels 14.

Figure 4:
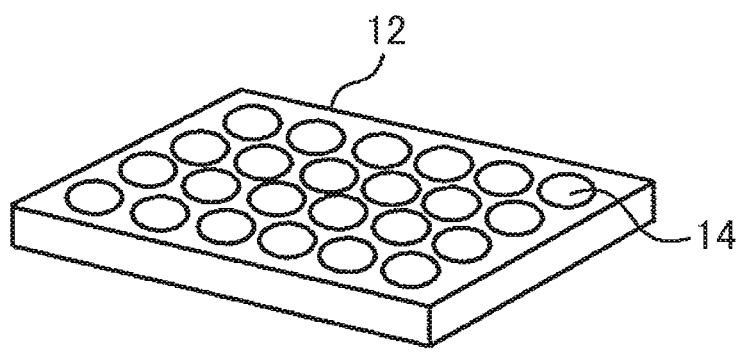
FIG. 4 is a diagram illustrating a first plate including a total of 24 vessels.

FIG. 4 is a diagram illustrating the microplate 12 including a total of 24 vessels 14. In the example illustrated in FIG. 4, the 24 vessels 14 are arrayed in 6 columns by 4 rows. It should be noted that in this case, the intermediate plate 13 has 24 convex portions 15. As described above, when the microplate 12 includes the plurality of vessels 14, cells can be cultured at the same time under different conditions.

Second Modification

The lid 11, the bottom surface 14A of each of the plurality of vessels 14, and the intermediate plate 13 have desirably substantially the same optical characteristic. Specifically, the lid 11, the bottom surface 14A of each of the plurality of vessels 14, and the intermediate plate 13 may be formed of a material having the same refractive index. In this way, it is possible to prevent the deformation of a target to be observed due to the refraction of the light between the configuring elements and to prevent the lowering of the accuracy of the turbidity measurement.

Third Modification

In the above description, the surface of the intermediate plate 13 substantially comes into contact with the lid 11, but the entire surface of the intermediate plate 13 is not necessarily required to come into contact with the lid 11. The shape of the lid 11 and the intermediate plate 13 is the shape that prevents dew condensation on the lid 11 due to the adherence of the evaporated culture medium 18.

Second Embodiment

In the configuration of the culturing device 1 of the first embodiment, the intermediate plate 13 having the convex portions 15 and the through holes 16 is sandwiched between the lid 11 and the microplate 12. On the contrary, a culturing device of a second embodiment is different from the culturing device 1 of the first embodiment in that in place of sandwiching the intermediate plate 13, a component having light transmittance is attached into each of the vessels 14.

FIG. 5 is a diagram of assistance in explaining the configuration of a culturing device 2 of the second embodiment. The culturing device 2 according to the second embodiment includes, in place of the typical microplate 12, a microplate in which a component 23 having light transmittance is attached into each of the vessels 14 included in the microplate 12 described in the first embodiment. A material of the component 23 can be selected from the same material as the material forming the lid 11, the microplate 12 and the intermediate plate 13 described in the first embodiment.

FIG. 5(a) is a perspective view of assistance in explaining each of the vessels 14 included in the microplate. The component 23 illustrated in FIG. 5(a) is bonded to the vessel 14. As illustrated in FIG. 5(a), the component 23 has a substantially rectangular parallelepiped shape, and has a curved surface coming into contact with the surface of the interior of the vessel 14.

FIG. 5(b) is a diagram illustrating the upper surface of each of the vessels 14 into which the component 23 is attached. As illustrated in FIG. 5(b), the component 23 is designed to have a size in which the upper opening end of the vessel 14 is not closed, and a surface of the component 23 on the opposite side of the curved surface of the component 23 coming into contact with the vessel 14 is located near the center of the vessel 14. Therefore, like the microplate 12, the vessel 14 included in the microplate has the opening 17. The culturing device 2 according to the second embodiment also enables the injection and suction of the liquid from the opening 17.

FIG. 5(c) is a side cross-sectional view of the culturing device 2 in which the lid 11 and the microplate are overlapped. As illustrated in FIG. 5(c), the component 23 has a surface 23A and a surface 23B substantially parallel to the bottom surface 14A of each of the vessels 14, and the component 23 is attached at a position where the surface 23A substantially comes into contact with the lid 11. That is, the surface 23A of the component 23 is located at the same height as the upper surface of the microplate or at the position slightly higher than the upper surface of the microplate.

When the component 23 is attached so that the surface 23A of the component 23 is located at the same height as the upper surface of the microplate, the lid 11 comes into contact with the microplate and the surface 23A of the component 23 so as to close the opening 17 of the vessel 14. In this case, a portion of the lid 11 coming into contact with the surface 23A is not fogged due to the occurrence of dew condensation.

Also, when the component 23 is attached so that the surface 23A of the component 23 is higher than the upper surface of the microplate, the lid 11 comes into contact with the surface 23A of the component 23, and covers the opening 17 of the vessel 14 without closing the opening 17. Also in this case, the portion of the lid 11 coming into contact with the surface 23A is not fogged due to the occurrence of dew condensation. It should be noted that although in this case, the opening 17 of the vessel 14 is not completely closed, there is no change to the fact that the lid 11 covers above the opening 17, so that the inclusion of any foreign substances can be prevented. Also, since a gap between the opening 17 and the lid 11 is sufficiently small, the culture medium 18 in the interior of the vessel 14 is hardly evaporated.

For example, the size of the component 23 is adjusted so that the surface 23B of the component 23 is immersed into the culture medium 18. In this way, the fogging of the surface 23B of the component 23 due to dew condensation can be prevented, so that the interior of the vessel 14 can be observed satisfactorily, and the measurement accuracy of turbidity can be improved.

It should be noted that as in the case with the first embodiment, the lid 11, the bottom surface 14A of the vessel 14 and the component 23 preferably have substantially the same optical characteristic. Also, the microplate can include an arbitrary number of vessels 14.

Third Embodiment

In the culturing device 2 of the second embodiment, the component 23 having light transmittance is bonded to the interior of each of the vessels 14. A culturing device 3 of a third embodiment is different from the culturing device 2 of the second embodiment in that a component 24 having light transmittance is pressed or fitted into the interior of the vessel 14.

FIG. 6 is a diagram of assistance in explaining the configuration of the culturing device 3 according to the third embodiment. The culturing device 3 includes a microplate in which the component 24 having light transmittance is attached into each of the vessels 14 included in the microplate 12 described in the first embodiment.

The component 24 has a substantially rectangular parallelepiped shape, and has, at both ends, curved surfaces that can come into contact with the inner surface of the vessel 14. A diameter of the component 24 is designed to be slightly larger than an inside diameter of the vessel 14. Therefore, when the component 24 is pressed into the vessel 14, the position of the component 24 can be fixed. A material of the component 24 can be selected from the same material as the material forming the lid 11, the microplate 12 and the intermediate plate 13 described in the first embodiment.

FIG. 6(a) is a perspective view of assistance in explaining each of the vessels 14 included in the microplate. The component 24 illustrated in FIG. 6(a) is pressed into the vessel 14. FIG. 6(b) is a diagram illustrating the upper surface of the vessel 14 into which the component 24 is attached.

As illustrated in FIG. 6(b), the component 24 is designed to have a size and a shape so that the upper opening end of each of the vessels 14 is not closed and the position of the component 24 can be fixed when the component 24 is pressed into the vessel 14. Therefore, like the microplate 12, the vessel 14 included in the microplate has the opening 17. The culture vessel 2 according to the second embodiment also enables the injection and suction of the liquid from the opening 17.

FIG. 6(c) is a diagram illustrating a state where an antibacterial agent 25 is coated onto the bottom surface in the interior of each of the vessels 14 in freeze-dried state. The antibacterial agent 25 is desirably coated onto the bottom surface of the vessel 14 before the component 24 is pressed into the vessel 14. When the culture medium 18 is injected from the opening 17 into the vessel 14, the antibacterial agent 25 is dissolved to prepare the culture medium 18 and the antibacterial agent 25 necessary for conducting an antibacterial susceptibility test at appropriate concentration. As described above, the antibacterial agent 25 or the culture medium 18 in freeze-dried state is previously accommodated in the interior of the vessel 14, so that by adding the necessary liquid, the culturing of cells can be easily started.

FIG. 6(d) is a cross-sectional view of the culturing device 3 in which the lid 11 and the microplate are overlapped. As illustrated in FIG. 6(d), the component 24 has a surface 24A and a surface 24B substantially parallel to the bottom surface 14A of each of the vessels 14, and the component 24 is attached at the position where the surface 24A substantially comes into contact with the lid 11. That is, like the component 23, the surface 24A of the component 24 is located at the same height as the upper surface of the microplate or at the position slightly higher than the upper surface of the microplate.

For example, a length of the component 24 is adjusted so that the surface 24B of the component 24 is immersed into the culture medium 18. In this way, the fogging of the surface 24B of the component 24 due to dew condensation can be prevented, so that the interior of the vessel 14 can be observed satisfactorily. As a result, the measurement accuracy of turbidity can be improved.

It should be noted that like the second embodiment, the lid 11, the bottom surface 14A of the vessel 14 and the component 24 preferably have substantially the same optical characteristic. Also, the microplate can include an arbitrary number of vessels 14. The attaching position of the component 24 is preferably the position suitable for the observation of the interior of the vessel 14.

Fourth Modification

FIG. 7 is a diagram illustrating another example of the component 24 pressed into each of the vessels 14. In a component 26 illustrated in FIG. 7, protrusions 26b extend in four directions from a center portion 26a in a cylindrical shape. That is, unlike the component 24, the component 26 is configured to thrust in two directions, and the opening 17 that the vessel 14 has is divided into four. The vessel 14 into which the component 26 is pressed enables the injection and suction of the liquid from the opening 17.

Also, like the component 24, the component 26 is designed so that a diameter of the component 26 is slightly larger than the diameter of the interior of the vessel 14, and can be pressed or fitted into the vessel 14. The component 26 has an upper surface and a lower surface substantially parallel to the bottom surface 14A of the vessel 14, and the component 26 is attached at a position where the upper surface of the component 26 substantially comes into contact with the lid 11. That is, like the component 24, the upper surface of the component 26 is located at the same height as the upper surface of the microplate or at the position higher than the upper surface of the microplate. As the material of the component 26, the same material as the material of the component 24 can be selected.

The center portion 26a of the component 26 is cylindrical, and the component 26 makes an observation region when the optical measurement is performed wider than the component 24. Also, the component 26 makes the opening 17 narrower than the component 24, so that the liquid is hard to be spilled when the culturing device 3 is conveyed.

Figure 8:
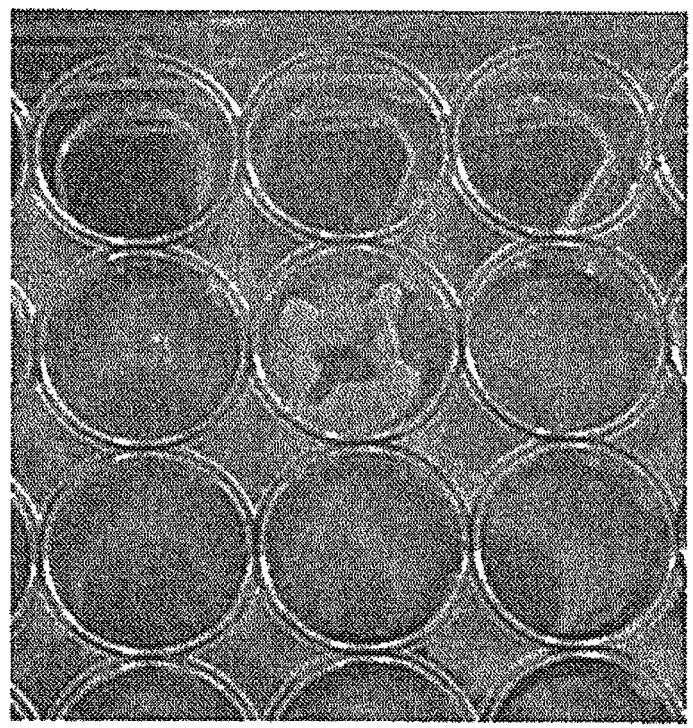
FIG. 8 is a diagram of assistance in explaining a state where the component prevents dew condensation on a lid.

FIG. 8 is a diagram of assistance in explaining a state where the component 26 prevents dew condensation on the lid 11. In FIG. 8, each of the vessels 14 shown at an upper portion is the vessel 14 into which the culture medium 18 is not injected, the vessel 14 shown at a center of a middle portion is the vessel 14 into which the component 26 is attached, and each of other vessels 14 is the conventional vessel 14 into which the culture medium 18 is injected. As illustrated in FIG. 8, it is found that in the case of the vessel 14 into which the component 26 is attached, the lid 11 is not fogged at a portion located above the component 26. Although not illustrated, likewise, in the case of the vessel 14 into which the component 23 is attached, the lid 11 is not fogged at the portion of the lid 11 located above the component 23, and in the case of the vessel 14 into which the component 24 is attached, the lid 11 is not fogged at the portion of the lid 11 located above the component 24. Also, likewise, in the first embodiment, the lid 11 is not fogged at the portion of the lid 11 located above the convex portion 15 included in the intermediate plate 13.

Fifth Modification

The culturing device may be provided in a state where an antibacterial agent 27 that is frozen is accommodated in each of the vessels 14. In that case, the antibacterial agent 27 in the culturing device that is freeze-kept is dissolved at room temperature, and by adding the necessary culture medium 18 and specimen, a medium suitable for the antibacterial susceptibility test can be prepared. It should be noted that, not only the antibacterial agent 27, but also the culture medium 18 and other chemical agents, may be accommodated in frozen state.

Figure 9:
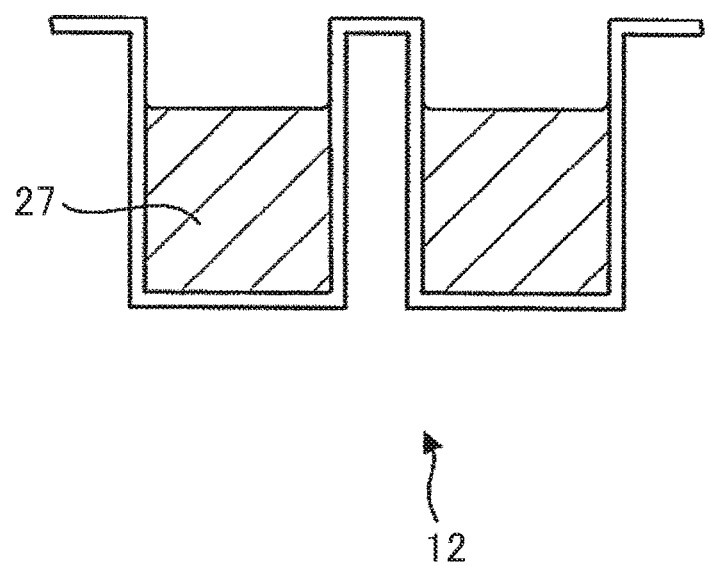
FIG. 9 is a diagram illustrating the first plate in which a frozen antibacterial agent is accommodated in the vessels.

FIG. 9 is a diagram illustrating the microplate 12 in which the antibacterial agent 27 and the culture medium 18 in frozen state are accommodated. When the antibacterial agent 27 and the culture medium 18 in frozen state are previously accommodated in the microplate 12, for example, after they are unfrozen at room temperature, as illustrated in FIG. 1(c), the intermediate plate 13 and the lid 11 are overlapped with the microplate 12, so that the culturing of cells can be easily started.

It should be noted that this disclosure is not limited to the above embodiments, and includes various modifications. For example, the above embodiments have been described in detail to simply describe the present invention, and do not necessarily include all the described configurations. Also, part of the configuration of one embodiment can be replaced with the configurations of other embodiments, and in addition, the configuration of one embodiment can be added with the configurations of other embodiments. Also, part of the configuration of each of the embodiments can be subjected to addition, deletion, and replacement with respect to other configurations.

LIST OF REFERENCE SIGNS 1, 2, 3 . . . Culturing device
11 . . . Lid
12A, 12B, 12C . . . Microplate
13 . . . Intermediate plate
14 . . . Vessel
15 . . . Convex portion
16 . . . Through hole
17 . . . Opening
18 . . . Culture medium
20 . . . Dichroic mirror
23, 24, 26 . . . Component
25 . . . Antibacterial agent
26a . . . Center portion
26b . . . Protrusion
27 . . . Antibacterial agent in frozen state All publications and Patent Literature cited in the present specification are incorporated herein by reference in their entirety.

The invention claimed is:

1. A culturing device comprising:
a microplate including a plurality of vessels for accommodating a culture medium, each of the plurality of vessels having a bottom surface have light transmittance and having a component attached to an inner surface thereof and extending inward toward an inside of the vessel, the component having light transmittance and extending from an upper end of the vessel to an interior of the vessel; and
a lid having light transmittance covering an upper surface of the microplate,
wherein the component has two flat surfaces parallel to the bottom surface of the vessel, one of the two surfaces being located at the same height as a highest portion of an upper opening of the vessel or at a position higher than the upper surface of the microplate, and
wherein the other of the two surfaces of the component is immersed into the culture medium accommodated in the vessel and contacts the culture medium accommodated in the vessel.

2. The culturing device according to claim 1,
wherein in the interior of each of the plurality of vessels, an antibacterial agent in freeze-dried state is accommodated.

3. The culturing device according to claim 1,
wherein in the interior of each of the plurality of vessels, an antibacterial agent or a culture medium ingredient in frozen state is accommodated.

4. The culturing device according to claim 1,
wherein the microplate includes 24 or more vessels.

5. The culturing device according to claim 1, wherein the component is bonded and attached into the vessel.

6. The culturing device according to claim 1, wherein the component is pressed and attached into the vessel.

7. The culturing device according to claim 1, wherein each component of each vessel protrudes inward off the inner surface of the vessel, the inner surface of the vessel contacting the culture medium accommodated in the vessel.

* * * * *